United States Patent [19]

McKendry et al.

[11] Patent Number: 4,645,852

[45] Date of Patent: Feb. 24, 1987

[54] ONE STEP CONVERSION OF EPOXYALKANES TO ALKYL ESTERS OF ALKYL AND ARYL SULFONIC ACIDS

[75] Inventors: Lennon H. McKendry; Richard C. Krauss, both of Midland, Mich.

[73] Assignee: The Dow Chemical Company, Midland, Mich.

[21] Appl. No.: 776,244

[22] Filed: Sep. 16, 1985

[51] Int. Cl.[4] .................. C07C 143/68; C07C 33/22; C07C 103/22
[52] U.S. Cl. ........................................ 558/49; 558/51; 558/50; 558/48; 564/170; 568/812; 568/437; 568/436; 568/426; 568/424; 568/442
[58] Field of Search ............... 260/456 R, 456 P; 558/49, 51; 564/170; 568/812, 426

[56] References Cited

U.S. PATENT DOCUMENTS 3,900,509  8/1975  Markley ...................... 260/456 R
3,954,440  5/1976  Markley ...................... 71/103
4,211,549  7/1980  Markley et al. ............. 71/88

OTHER PUBLICATIONS

Weissberger, Chemistry of Heterocyclic Compounds, vol. 19, Part I, 1964, pp. 382–384.

*Primary Examiner*—Nicky Chan
*Attorney, Agent, or Firm*—Thomas R. Savitsky; Edward E. Schilling

[57] ABSTRACT

In an improved process of converting a 1,2-epoxy-2-phenylbutane or a 1,2-epoxy-2-phenylpentane to a 2-hydroxy-2-phenylbutylsulfonate, sulfamate, or halide, or the corresponding 2-hydroxy-2-phenylpentyl compound, respectively, by the reaction at about 40° to 120° C. in the presence of an organic solvent of the requisite epoxybutane or epoxypentane with a proton source and a nucleophile. The proton source can be a free strong acid such as a sulfonic, sulfamic acid, or hydrohalide acid, or the proton source can be derived from an equilibrium system comprising a free strong acid and weak base in equilibrium with the respective deprotonated strong acid and protonated weak base. The process is carried out in one step with reduction or avoidance of aldehyde formation by rearrangement of the epoxyalkane.

36 Claims, No Drawings

ONE STEP CONVERSION OF EPOXYALKANES TO ALKYL ESTERS OF ALKYL AND ARYL SULFONIC ACIDS

BACKGROUND OF THE INVENTION

Certain 2-hydroxy-2-phenylbutyl-sulfonate and 2-hydroxy-2-phenylbutylsulfamate compounds have been described in U.S. Pat. Nos. 3,900,509 and 3,954,440. These compounds are active herbicides. Some related substituted alkylsulfonate and alkylsulfamate compounds are also useful in enhancing the activity of triazine herbicides.

The substituted butyl sulfonate, substituted butyl sulfamate, substituted pentylsulfonate and substituted pentyl sulfamate compounds may be prepared from the requisite alpha-substituted styrenes as described in said U.S. patents in which the styrene compound is first converted to a diol and is then mono-esterified with the requisite substituted sulfonic acid or sulfamic acid.

However, it is more economical under some circumstances to prepare the desired sulfonates and sulfamates from the corresponding epoxybutanes and epoxypentanes. These epoxyalkane compounds are prepared from the requisite α-substituted styrenes in accordance with the methods of U.S. Pat. No. 4,211,549.

Methods of preparation from the epoxyalkanes have heretofore required the use of several process steps.

FIELD OF THE INVENTION

The invention relates to an improved process of converting a 1,2-epoxy-2-phenylbutane or a 1,2-epoxy-2-phenylpentane to a 2-hydroxy-2-phenylbutylsulfonate, sulfamate, or halide, or the corresponding 2-hydroxy-2-phenylpentyl compound, respectively, each compound having a substituted sulfonate, sulfamate, or halo group, as the case may be, in the 1-position on the alkane chain.

DESCRIPTION OF THE PRIOR ART

The reaction of epoxides with sulfonic acids is described in the literature, for example, in the text by Arnold Weissberger, *Chemistry of Heterocyclic Compounds*, Vol. 19, Part I, 382–384, (1964), and in references cited therein. However, so far as is known, none of the references deals with the problem here described and solved, viz., the problem of aldehyde formation.

SUMMARY OF THE INVENTION

It has now been found that on reacting a 1,2-epoxy-2-phenylbutane or a 1,2-epoxy-2-phenylpentane, of a class more fully defined hereinafter, with a proton source and with a nucleophile in an organic solvent medium and at a temperature in the range of about 20° to about 120° C., there is obtained in good yield a 2-hydroxy derivative of the epoxy compound with the nucleophile attached to the 1-position of the butane or pentane chain, while from substantially none to a moderate amount of the aldehyde is formed.

A sufficient amount of the proton source must be present to protonate the epoxide ring, thereby catalyzing ring opening. In addition, if the concentration of the nucleophile in the reaction mixture is insufficient, aldehyde formation is extensive and aldehyde will be the predominant product.

More specifically the present invention is concerned with a method of preparing a 2-hydroxybutyl or 2-hydroxypentyl compound of the following formula:

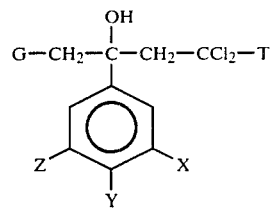

wherein:
T is F, Cl, Br, CH$_3$, CF$_3$ or

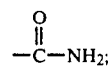

X, Y and Z are each independently H, F, Cl, Br, CH$_3$, C$_2$H$_5$, or CF$_3$, provided that when Y is other than H, at least one of X and Z must be other than H;

G is R$^1$SO$_2$O—; R$^2$R$^3$NSO$_2$O—; Br; Cl; F; or I;

R$^1$ is C$_1$–C$_{18}$ alkyl; C$_1$–C$_8$ haloalkyl; C$_3$–C$_6$ cycloalkyl; benzyl; naphthyl; phenyl; monovalent radical of monocyclic heterocyclic ring having ring atoms selected from the group consisting of carbon and at least one of nitrogen, sulfur and oxygen; monovalent radical of bicyclic heterocyclic fused ring having ring atoms selected from the group consisting of carbon and at least one of nitrogen, sulfur and oxygen; and any of phenyl, benzyl, naphthyl, said monocyclic heterocyclic radical or bicyclic heterocyclic fused ring radical in which up to three ring hydrogens have been replaced by substituent groups which may be the same or different and are selected from the group consisting of methyl, methoxy, substituted methoxy, methylthio, chloro, bromo, fluoro, CF$_3$ or nitro; and R$^2$ and R$^3$ are each independently H, C$_1$ to C$_4$ alkyl, C$_1$ to C$_4$ hydroxyalkyl, and C$_3$ to C$_6$ alkoxyalkyl, provided if either is C$_1$ to C$_4$ hydroxyalkyl or C$_3$ to C$_6$ alkoxyalkyl the other must be H, which comprises:
reacting during a reaction period at a temperature in the range of about 20° to about 120° C. in the presence of an organic solvent an epoxide compound of the following formula:

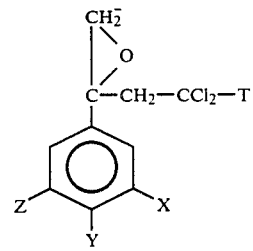

wherein:
T, X, Y and Z are as defined hereinabove;
with a proton source that is strong enough to protonate and catalyze the opening of the oxirane ring of said epoxide compound;

and with a nucleophile, the nucleophile being an anion and is selected from the group consisting of R$^1$SO$_2$O$^\ominus$; R$^2$R$^3$NSO$_2$O$^\ominus$; Cl$^\ominus$; Br$^\ominus$; F$^\ominus$; or I$^\ominus$;
wherein R$^1$, R$^2$ and R$^3$ are as defined hereinabove;

the nucleophile being present in sufficient amount that substantial reaction takes place at the reaction temperature sufficient to avoid formation of more than about 50 mole percent of the theoretical maximum amount of an aldehyde compound of the following formula:

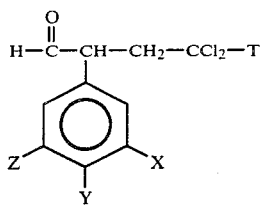

wherein T, X, Y, and Z are as defined hereinabove;

and said proton source provided throughout the reaction period in an amount sufficient to catalyze ring opening and facilitate reaction to form the desired 2-hydroxybutyl or 2-hydroxypentyl compound. The proton source can be, for example, a free strong acid such as a substituted sulfonic acid, a substituted sulfamic acid, hydrogen chloride, hydrogen bromide, hydrogen fluoride or hydrogen iodide, or the proton source can be derived from an equilibrium system comprising a free strong acid and a non-nucleophilic weak base in equilibrium with the respective deprotonated strong acid and protonated weak base.

DETAILED DESCRIPTION OF THE INVENTION

As indicated hereinabove the present improved process provides for the one-step conversion of epoxides of the class described to one of a sulfonate, sulfamate, or halide derivative in which such substituted group is appended to the terminal alkane carbon of the butane or pentane compound, with very little aldehyde formed by rearrangement of the epoxide.

It is desired not to be bound by the following explanation, but the general reaction sequence is believed to be illustrated by the following diagrammatic equations describing steps I and II:

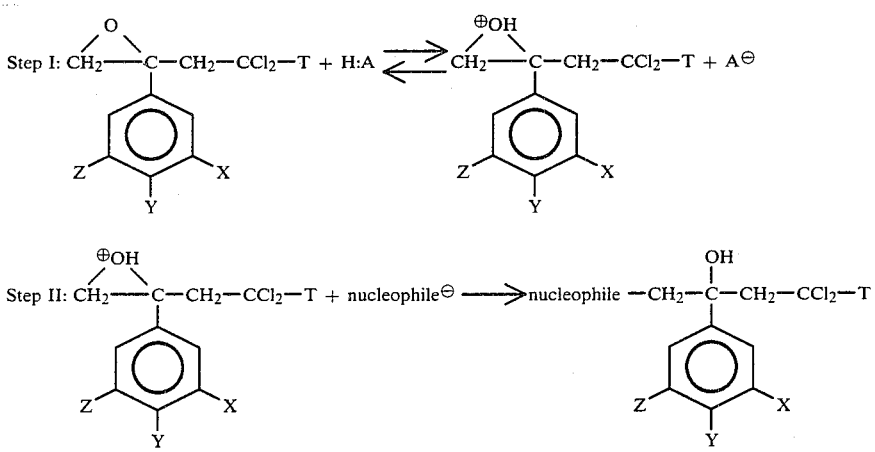

in which $R^1$, X, Y, Z and T have the meaning set forth hereinabove, and H:A represents the proton source.

As seen in Step I, the proton from the proton source attacks the epoxide ring protonating the oxygen and weakening the O—C bonds. In Step II, the nucleophile completes the attack, the anionic nucleophile attaching to the CH$_2$ group and the hydrogen of the catalyzing proton source attaching to the epoxy oxygen.

As indicated above, in the absence of sufficient concentration of the nucleophile, the protonated epoxide ring will open and preferentially rearrange to afford the undesired aldehyde, the rearrangement being indicated in the following equation:

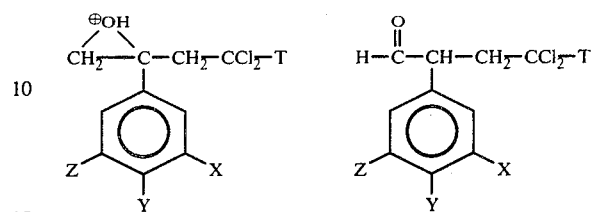

Aldehyde formation is favored when an insufficient amount of a nucleophile is present that is capable of reacting promptly with protonated epoxide before rearrangement to the aldehyde can occur.

At temperatures above about 120° C., the desired product is subject to shedding the nucleophile and rearranging to the epoxide compound used as starting material and other by-products.

The proton source can be most any strong acid (e.g., a free acid or a conjugate acid) which will catalyze the weakening and opening of the epoxide ring. Suitable strong acids for use as a proton source typically have the characteristics of providing a very low pH, below about 4, preferably below about 2, if taken up alone to form an aqueous solution. In addition, the salt of any suitable free strong acid can serve as a nucleophile and the acid form of the nucleophile (i.e., free strong acid) desired for addition to the butane or pentane epoxide compound to be modified can be used as a proton source. Otherwise, the salt form of the free strong acid will compete with the desired nucleophile in reacting with the epoxide.

Thus, the preferred free strong acids are selected from the free acid form of the sulfonate or sulfamate nucleophile to be reacted with the epoxide compound unless one of the halide ions is to be the desired nucleophile, in which case the requisite hydrogen halide is used.

Suitable nucleophiles are those which will complete the attack of the epoxide ring and attach to the CH$_2$ group to form the desired compound, for example suitable sulfonates, sulfamates, or halides. The nucleophile must be in anionic form; for example the nucleophile can be added to the reaction in salt form. However, when the sole proton source is selected from the free acid form of the nucleophile, it is preferred to employ a strong base which reacts with the free acid in order to generate the anionic form of the free acid (i.e., the nucleophile).

The following reaction sequence (Steps IV and V) is believed to illustrate the present invention when the proton source is the free acid form of the nucleophile and a strong base is employed which reacts with the free acid to form the nucleophile:

monium bromide and tetrabutylammonium chloride or crown ethers such as 18-crown-6, dicyclohexyl-18-crown-6 or diphenyl-18-crown-6. The quaternary ammonium halides can also be used as the source of the nucleophile for halohydrin formation.

In another embodiment of the present invention, the proton source can be derived from an acid-base equilibrium system. When a free strong acid and a non-nucleophilic weak base are employed together in a reaction mixture, an equilibrium system is created with the respective deprotonated strong acid and protonated weak

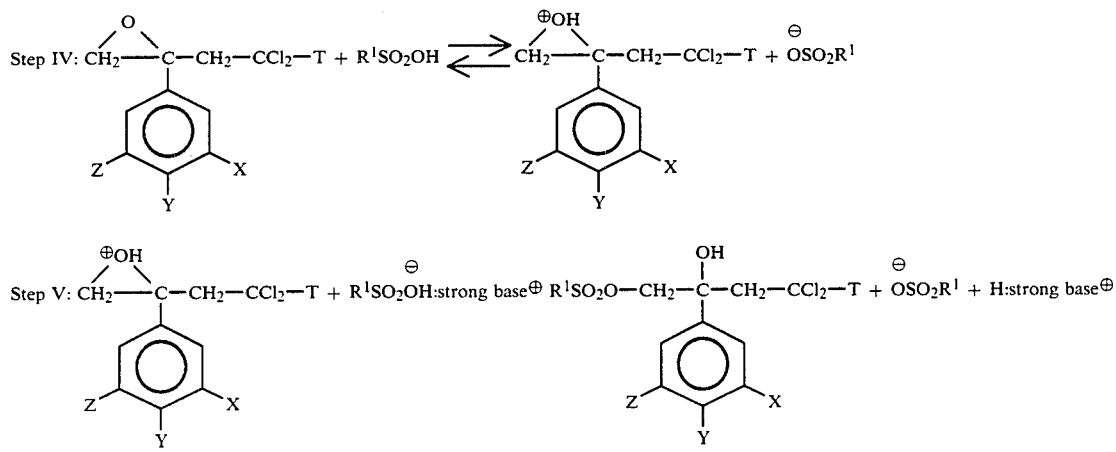

As seen in Step IV, the free stong acid attacks the epoxide ring protonating the oxygen and weakening the O—C bonds. In Step V, the nucleophile completes the attack, the anionic $R^1SO_2O^\ominus$ group attaching to the $CH_2$ group and the hydrogen (i.e., proton) of the catalyzing free strong acid attaching to the epoxy oxygen, leaving an anionic $O^\ominus SO_2R^1$ group and a cationic H:strong$^\oplus$ base group which again associate as illustrated in the following equation, Step VI:

Step VI:

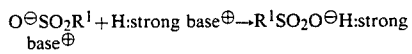

$O^\ominus SO_2R^1 + H:strong\ base^\oplus \rightarrow R^1SO_2O^\ominus H:strong\ base^\oplus$ Relatively strong bases which work well in the present reaction described in Steps IV, V and VI include tertiary amines, such as a triloweralkylamine, e.g., triethylamine, trimethylamine, pyridine or dimethylaminopyridine, and alkali metal hydroxides, such as NaOH and KOH or an alkali metal carbonate such as Na$_2$CO$_3$, the alkali metal salts being used in the presence of quaternary ammonium compounds such as phenyltrimethylammonium chloride, benzyltriethylambase. For this embodiment of the present invention, the deprotonated strong acid (now an anionic weak base) acts as a nucleophile, and the protonated weak base (now a cationic strong acid) acts as an additional proton source. The equilibrated acid-base system is then reacted with the epoxy compound under conditions such that a 2-hydroxy derivative of the epoxy compound with the nucleophile attached to the 1-postion of the butane or pentane chain is formed. The pK$_a$ of the free strong acid and the pK$_b$ of the non-nucleophilic weak base should be within about one unit of each other in order to form a suitable acid-base system. By use of an equilibrium system, both the free strong acid and the conjugate strong acid may protonate the eopxide ring, the relative contribution of each such acid being dependent upon the relative pK$_a$ and pK$_b$ of the respective free strong acid and weak base.

The following reaction sequence (Steps VII, VIII and IX) is believed to illustrate the present invention when the proton source is derived from an acid-base equilibrium system:

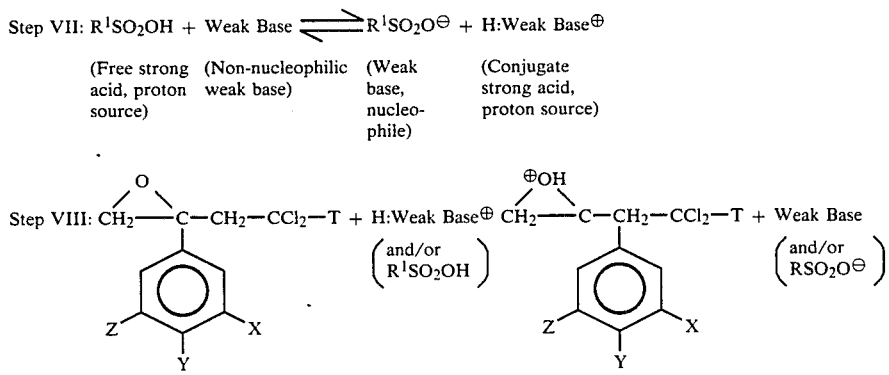

Step IX: 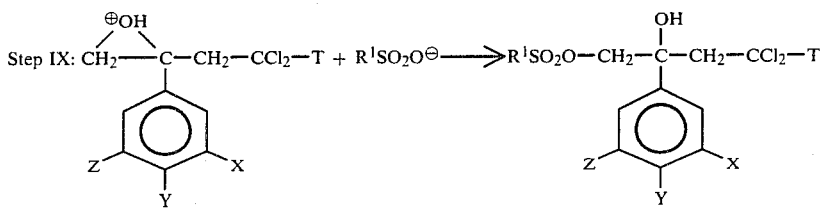

wherein $R^1$, X, Y, Z and T have the meaning set forth hereinabove.

As seen in Step VII, the free strong acid and non-nucleophilic weak base form an equilibrium system with the respective deprotonated strong acid (now an anionic weak base which acts as a nucleophile) and protonated weak base (now a cationic conjugate strong acid which may act as a proton source). In Step VII, the proton source attacks the oxirane ring protonating the oxygen and weakening the O—C bonds. In Step IX, the nucleophile completes the attack, with the nucleophilic $R^1 SO_2O^\ominus$ group attaching to the $CH_2$ group and the hydrogen (i.e., proton) of the catalyzing proton source attaching to the epoxy oxygen.

The mode of action of other types of strong acids and their corresponding deprotonated nucleophiles is belived to be similar to that of the sulfonic acid and sulfonate anion illustrated in Steps VII, VIII, and IX.

It is important that the weak base employed in Steps VII and VIII is non-nucleophilic. If the weak base is nucleophilic, then it could compete with the deprotonated strong acid nucleophile resulting in unwanted substitutions occurring on the epoxy compound.

The non-nucleophilic weak base employed must be weak enough with respect to the free strong acid to form an equilibrium with the anion of the free strong acid and provide a reservoir of free acid in limited amount for the desired reaction. It is essential that the $pK_a$ of the free strong acid and the $pK_b$ of the non-nucleophilic weak base are no greater than about one unit apart. If the respective $pK_a$ and $pK_b$ are greater than about one unit apart, then an insufficient equilibrium will result and the reaction will be driven too far either to the right or the left depending upon whether the $pK_a$ or $pK_b$ is greater. Therefore, when using the acid-base equilibrium system as a proton source it is preferred that the $pK_a$ of the free strong acid and the $pK_b$ of the non-nucleophilic weak base are about equal.

As discussed above, a non-nucleophilic weak base which has a $pK_b$ no greater than about one unit apart from the free strong acid employed is suitable to result in the desired reaction. Non-nucleophilic weak bases which are suitable depending on which free strong acid is employed include diphenyl amine; tetraalkylureas such as tetramethyl urea; dialkylamides such as dimethylformamide, N-methyl-2-pyrrolidone, dimethyl acetamide, and N-formylmorpholine; lower alkyl phosphates such as tributyl phosphate; dimethylsulfone; tetramethylenesulfone; and hexamethylphosphoric triamide. Preferred non-nucleophilic weak bases are the dialkylamides and most preferred is dimethylformamide.

The sulfonic acids usable according to the invention are synthesized according to methods described in the journal article by L. Field, "Some Recent Developments in Synthetic Organic Sulfur Chemistry", published in Synthesis, pp. 101–133 (1972) and in references cited in the article.

The suitable sulfamic acids may be synthesized according to methods described (1) in the text *Sulfonation Related Reactions*, Chapter 7, E. E. Gilbert, Interscience Publishers, Division of John Wylie & Sons, New York, 1965; (2) in the paper by T. I. Bieber, J. Am. Chem. Soc., 75 1405–1408 (1953); and (3) in the paper by C. D. Hurd and N. Kharasch, J. Am. Chem. Soc., 69 2113–2115(1947).

The process of the present invention is rather readily carried out in a manner that less than about 50 mol percent of the maximum theoretical amount of the aldehyde is formed. Preferably, the reaction is carried out so that less than about 25 mol percent of possible aldehyde is formed, and even more preferably that less than 15 mol percent of the possible theoretical maximum amount of aldehyde is formed.

When a free strong acid is employed as the proton source and a strong base is employed (as illustrated in Steps IV, V and VI), aldehyde formation can be avoided or minimized by controlling the ratio of free strong acid to nucleophile present. This can be accomplished by adding the free strong acid to the reaction mixture over a period of time during which the protons are consumed steadily in the reaction.

In using the acid-base equilibrium system as a proton source, aldehyde formation is minimized since the acid-base equilibrium system provides a steady supply of the proton source as the reaction proceeds, substantially without generating such a high concentration of protonated epoxide with respect to the concentration of the nucleophile as to favor aldehyde formation.

The free strong acids for use in the acid-base equilibrium system are selected from the free acid form of the sulfonate or sulfamate nucleophile to be reacted with the epoxide compound unless one of the halide ions is to be the desired nucleophile, in which case the requisite hydrogen halide is used.

Generally, the reaction of the present invention is completed in about 1 to about 6 hours at a temperature in the range of about 20° to about 120° C., preferably in the range of about 40° to about 110° C., and, most preferably about 70° to 110° C., whereby the reaction can be completed in most instances in about 1 to 4 hours.

The process of the present invention must be carried out in an organic solvent medium which provides enough solvency for the nucleophile (because of its ionic properties) to participate in the reaction with the protonated epoxide ring so that the reaction can proceed at a practical rate at a reasonable reaction temperature. When employing the acid-base equilibrium system, the reaction can be carried out in excess non-nucleophilic weak base wherein said weak base also acts as a solvent. However, the reaction, regardless of which embodiment is employed, is conveniently carried out in the presence of an inert organic solvent.

In general, suitable inert solvents for use as a reaction medium include acetonitrile, toluene, xylene, benzene, carbon tetrachloride, cyclohexane, chloroform and methylene chloride. The preferred inert solvent media are benzene, toluene and acetonitrile.

It is essential for complete reaction of the epoxide compound that at least one equivalent of proton source per equivalent of the epoxide compound be provided or generated so that an equivalent of proton source is provided during the course of the reaction to catalyze the essential opening of the epoxide ring. It is also essential to provide or generate at least one equivalent of the nucleophile per equivalent of the epoxide compound during the course of the reaction to form the desired product and prevent aldehyde formation. The amount of nucleophile in excess of one equivalent per equivalent of epoxide compound is not critical. A large excess of nucleophile can be present and the reaction can still proceed satisfactorily. The only constraints placed upon the amount of nucleophile in excess of one equivalent are that of economics and convenience.

While the reaction mixture need not be anhydrous, is is preferred to minimize or avoid the presence of water which is believed to have the effect of taking up the strong acid and hindering its transfer into the solvent medium and of reacting with the epoxide to afford the diol.

In carrying out the present improved process with initial addition of all the reactants, it is preferred to employ from about 1 to about 3 equivalents of the proton source (i.e., free strong acid and/or conjugate strong acid) per equivalent of epoxide compound employed. When a strong base is employed, from about 0.5 to 2 equivalents of strong base per equivalent of epoxide compound are also added. The ratio of equivalents of free strong acid to equivalents of strong base is in the range of about 1.25 to about 4, preferably about 1.5 to about 3. When a weak base is employed (i.e., in the acid-base equilibrium system) at least 0.5 equivalents of weak base per equivalent of epoxide compound are also added. The ratio of equivalents of weak base to equivalents of free strong acid is at least 1.0 and preferably at least 1.5. As mentioned hereinabove, the weak base may be present in such an excess so as to also serve as a solvent medium for the reaction.

When a strong base is employed (as illustrated in Steps IV, V and VI) and all of the reactants are not added initially, the relative proportions of the reactants can vary. For example, when the free strong acid is added to the other reactants (i.e., epoxide compound and strong base) steadily or in frequent small additions over a period of about 1 to 4 hours (while the reaction mixture is maintained at reaction temperature), from about 0.05 to about 1 equivalents of strong base per equivalent of epoxide compound and from about 1 to 2 equivalents, preferably 1.1 equivalents of free strong acid per equivalent of epoxide compound are employed.

The reaction mixture is then held at the reaction temperature in the range above specified until substantially complete reaction has taken place.

The reaction mixture is then allowed to cool and, if desired, is diluted with from about 1 to 3 times the volume of the reaction mixture with a suitable solvent, e.g. the same solvent used as reaction medium, preferably about 2 volumes, and is then washed several times with a like amount of water, then with a similar volume of dilute (e.g., 5 percent by weight) solution of a base such as sodium bicarbonate and finally by a similar volume of dilute acid such as 10 percent by weight HCl solution (about 2.5 normal concentration).

The solvent layer is separated and dried, e.g., with anhydrous $Na_2SO_4$ and preferably treated with charcoal or activated carbon. Finally, the solvent is removed under reduced pressure, typically leaving a crystalline product, but occasionally an oil which crystallizes on standing, but sometimes must be taken up in a solvent such as methylcyclohexane and crystallized therefrom.

The following examples are presented by way of illustration and the scope of the invention is not intended to be limited thereto.

EXAMPLE 1

Comparison Run:

To a 25 ml round bottom flask was added 314.3 milligrams (mg) (0.9810 millimoles ("mmole")) of 4,4,4-trichloro-1,2-epoxy-2-(3,5-dichlorophenyl)butane, 234 mg (1.234 mmole) of p-toluenesulfonic acid monohydrate and 3 milliliters (ml) of acetonitrile. The mixture was stirred while at ambient temperature (24° C.) with periodic sampling for nuclear magnetic resonance (NMR) analysis. After 4 hours both 4,4,4-trichloro-2-(3,5-dichlorophenyl)-2-hydroxybutyl-1-(4-methylphenyl)-sulfonate and 4,4,4-trichloro-2-(3,5-dichlorophenyl)-butyraldehyde were observed but the bulk of the epoxybutane compound remained unreacted.

Further Comparison Run:

After 2 hours of the previous run a small sample of the reaction mixture was withdrawn while the run continued. The small sample was heated at 65° C. in an oil bath for 1.5 hours and then NMR analysis was carried out showing that all of the epoxybutane compound had reacted, much of it forming the butyraldehyde.

Experimental Run:

To the reaction mixture at hand at the end of the initial comparison run was added 217.4 mg (1.119 mmole) of sodium p-toluenesulfonate and about 100 mg of dicyclohexyl 18-crown-6 ether and stirring was continued for 24 hours. NMR analysis at that time showed that all of the epoxybutane compound had reacted, nearly all of the sulfonate compound with very little additional butyraldehyde forming after the 4 hour comparison run, i.e., prior to the addition of the sodium p-toluenesulfonate.

The reaction mixture was filtered and the solvent in the filtrate removed in vacuo. The residual oil was dissolved in $CCl_4$ and washed with 10 percent by weight $NaHCO_3$ solution and then with several portions of water. The $CCl_4$ layer was filtered through anhydrous $MgSO_4$ crystals into an NMR tube and assayed by NMR, showing that the product was about 73 molar percent desired sulfonate and about 27 percent undesired butyraldehyde.

EXAMPLE 2

Comparison A:

To a 100 ml round bottom flask was added 5 grams (g) (0.0148 mole) of 4,4,4-trichloro-1,2-epoxy-2-(3,5-dichlorophenyl) butane; 2.97 g (0.0156 mole) of sodium p-toluenesulfonate; 3.03 g (0.0156 mole) of p-toluenesulfonic acid; 0.5 g of phenyltrimethylammonium chloride and 50 ml of acetonitrile. The reaction mixture was stirred at ambient temperature for 4 hours. NMR analysis at that time showed only slight reaction of the epoxybutane compound to form some sulfonate and some aldehyde.

Experimental Run A:

The reaction mixture from Comparison A was heated to and maintained at reflux (i.e., about 80° C.). NMR analysis showed complete reaction of the epoxybutane starting material within 2 hours. After 3 hours the mixture was allowed to cool and stand overnight.

The cooled reaction mixture was filtered and the acetonitrile solvent removed in vacuo. The residual light yellow oil was taken up in 50 ml of methylene chloride and the solution washed once with 50 ml of 10 percent by weight aqueous $NaHCO_3$ and twice with 50 ml portions of water. The methylene chloride solution was dried with anhydrous magnesium sulfate, filtered, and the solvent flashed off in vacuo, affording 6.45 g of a viscous oil. NMR analysis showed the oil consisted of 34 mole percent butyraldehyde compound and 66 mole percent of the desired 4,4,4-trichloro-2-(3,5-dichlorophenyl)-2-hydroxybutyl-1-(4-methylphenyl) sulfonate.

The remaining oil was taken up at room temperature in 14 ml of methylcyclohexane and cooled to 5° C. and stirred whereupon 2.87 g of a white crystalline solid was recovered after washing the precipitate three times with 10 ml portions of pentane and air drying the crystals. The product exhibited a melting temperature of 108° to 109.5° C., and an NMR spectrum appropriate for the desired sulfonate.

Comparison B:

The same reactants in the same amounts were reacted as in Comparison A above, except that 0.5 g of 18-crown-6 ether was used in place of 0.5 g of phenyltrimethylammonium chloride to bring some of the sodium p-toluenesulfonate into reaction in the solvent phase. Again, NMR analysis after 4 hours showed only slight reaction of the epoxybutane compound to form some sulfonate and some aldehyde derivatives thereof.

Experimental Run B

The reaction mixture from Comparison B was then heated to reflux and reacted in the same manner as described in Comparison Run A for the composition used there.

The reaction mixture was also worked up in the same manner as in Comparison Run A with similar results except that the oil initially obtained was taken up in diethyl ether instead of methylene chloride. Again, the partly purified oil was taken up and reprecipitated from methylcyclohexane and the crystals obtained washed with pentane, yielding 2.53 g of a white solid having the appropriate NMR spectrum for the desired sulfonate compound and a melting temperature of 107.5° to 109.5° C.

EXAMPLE 3

In a series of three runs the following listed reactants and solvent media were employed as components in respective reaction mixtures:

| Component | Amount |
| --- | --- |
| Run A | |
| Epoxybutane | 0.2017 g (0.630 mmole) |
| p-TSA.H$_2$O | 0.1205 g (0.633 mmole) |
| Na—p-TS | 0.1264 g (0.651 mmole) |
| CH$_3$CN | 2 ml |
| PhMe$_3$NCl | 0.2076 g |
| Run B | |
| Epoxybutane | 0.2017 g (0.630 mmole) |
| p-TSA.H$_2$O | 0.2411 g (1.268 mmole) |
| K$_2$CO$_3$ | 0.0431 g (0.312 mmole) |
| CH$_3$CN | 2 ml |
| Run C | |
| Epoxybutane | 0.2006 g (0.626 mmole) |
| p-TSA.H$_2$O | 0.1217 g (0.640 mmole) |
| Na—p-TS | 0.1237 g (0.637 mmole) |
| CH$_3$CN | 1 ml |
| H$_2$O | 1 ml |

In the above tabulations: epoxybutane means 4,4,4-trichloro-1,2-epoxy-2-(3,5-dichlorophenyl)butane; p-TSA, H$_2$O means p-toluenesulfonic acid monohydrate; Na-p-TS means sodium p-toluenesulfonate; and PhMe$_3$NCl means phenyltrimethylammonium chloride.

In each case the components were heated together at 42°–45° C. for 4 hours and cooled. In Runs A and B the cooled reaction mixtures were filtered and the solvent removed from the filtrate by flashing off in vacuo. The oily residues were taken up in 0.5 ml of CCl$_4$ and the solution washed once with 5 ml of water, then with 5 ml of 10 percent by weight aqueous NaHCO$_3$ solution and then again with 5 ml of water. The CCl$_4$ solution was then filtered through anhydrous MgSO$_4$ and into respective NMR tubes for assay.

The cooled reaction mixture in Run C was diluted with about 7 ml H$_2$O and then extracted with about 0.5 ml CCl$_4$. The CCl$_4$ extract was washed with about 5 ml of 10 percent by weight aqueous NaHCO$_3$ solution and then with 5 ml H$_2$O before filtering through anhydrous MgSO$_4$ into an NMR tube for assay.

Then NMR spectra were run and the following determinations were made:

In Run A the epoxybutane compound was all reacted, but only about 5 mole percent of the sulfonate formed, the remainder being the chlorohydrin.

In Run B about half of the epoxybutane reacted and the products were the desired sulfonate and the undesired butyraldehyde in about equal amounts.

In Run C no reaction had occurred in the two-phase system.

EXAMPLE 4

Two runs, Run A and Run B, were carried out largely in parallel utilizing the method of the invention. The reactants and reaction media employed in the reaction mixtures are as follows:

| Components | Run A Amount | Run B Amount |
| --- | --- | --- |
| Epoxybutane | 10.0 g (0.0312 mole) | 10.0 g (0.0312 mole) |
| p-TSA.H$_2$O | 12.5 g (0.0657 mole) | 12.5 g (0.0657 mole) |
| CH$_3$CN | 50 ml | — |
| CH$_2$Cl$_2$ | — | 50 ml |
| (C$_2$H$_5$)$_3$N | 4.3 ml (0.0308 mole) | — |
| pyridine | — | 2.5 ml (0.0309 mole) |

In the above table epoxybutane and p-TSA.H$_2$O referred to the same compounds as those identified in Example 3.

In both runs the reactants and reaction media were placed in 100 ml round bottom flasks and heated and stirred for 24 hours, Run A at 50° C. and Run B at reflux.

Samples were removed from the reaction mixture of Run A at 6 hours and 16 hour intervals, respectively and analyzed. Analysis showed that the reaction was 55 percent and 82 percent complete at these times with an 87 to 13 molar ratio between the desired sulfonate product and butyraldehyde compound being formed.

After the 24 hour reaction period, the reaction mixture in the form of a yellow solution was cooled and the solvent removed in vacuo. The residual oil obtained was taken up in 100 ml of diethylether and the ether solution washed twice with 100 ml portions of water and once with a 100 ml portion of 10 percent by weight aqueous NaHCO$_3$ solution. The ether solution was then dried by filtering it through anhydrous MgSO$_4$ and the solvent removed from the filtrate in vacuo, affording 13.40 g of a yellow oil which crystallized on standing. An NMR analysis of a small sample of the oil showed that the reaction had been about 95 percent complete and that the molar ratio between the desired sulfonate compound and the undesired butyraldehyde compound was 9 to 1 in the product.

The remaining solid was taken up in 25 ml of methylcyclohexane and the solution cooled to 5° C., resulting in precipitation of a white solid which was collected by filtration and rinsed three times with 10 ml portions of n-pentane. The washed precipitate was air dried and 10.92 g of 4,4,4-trichloro-2-(3,5-dichlorophenyl)-2-hydroxybutyl-1-(4-methylphenyl)sulfonate was obtained having a melting point of 109° to 109.5° C. The yield was calculated to be 74.8 percent based on the amount of epoxybutane reactant.

In Run B the reaction mixture was cooled after 24 hours and diluted with 50 ml of additional methylene chloride, washed twice with 100 ml portions of water and once with a 100 ml portion of 10 percent by weight aqueous NaHCO$_3$ solution, then dried by filtration through an anhydrous MgSO$_4$ and the methylene chloride removed in vacuo, resulting in a yellow solid product. NMR analysis of occurred product showed that reaction was 93 percent complete and the ratio of desired sulfonate to butyraldehyde compound to be 9.4 to 0.6.

The remaining crude yellow product was taken up in methylcyclohexane and purified and recrystallized in the same manner as utilized in Run A, resulting in 11.2 g of white crystalline product (78.3% yield based on conversion) identical to that obtained in Run A, having a melting temperature of 109.5° to 110° C.

EXAMPLE 5

To a 100 ml round bottom flask was added 0.6567 g (0.00345 mole) of p-toluenesulfonic acid monohydrate, 0.0574 g (0.000334 mole) of phenyltrimethylammonium chloride, and 10 ml of acetonitrile, and heating at reflux was carried out for 15 minutes. Then 0.997 g (0.003112 mole) of 4,4,4-trichloro-1,2-epoxy-2-(3,5-dichlorophenyl)butane was added to the flask and the solution was heated at reflux for 3 hours. The reaction mixture was cooled and the solvent was removed in vacuo. The oily residue was taken up in 15 ml of CCl$_4$ and the solution washed twice with 10 ml portions of water and once with a 10 ml portion of 10 percent by weight aqueous NaHCO$_3$. The CCl$_4$ solution was dried by filtration through anhydrous MgSO$_4$ and NMR analysis was made upon a sample of the filtrate. The analysis showed that the reaction was substantially complete and that the molar ratio of desired sulfonate to undesired butyraldehyde compound was about 33 to 67.

The solvent was removed in vacuo and the oily residue taken up in 2 ml of methylcyclohexane and cooled to −10° C., resulting in the precipitation of a white solid. The supernatant solvent was removed with a filter stick. The precipitate was washed three times with 2 ml portions of n-pentane and dried in vacuo at 50° C., affording 0.2372 g of a white powder having a melting point of 109° to 110° C. and identified as 4,4,4-trichloro-2-(3,5-dichlorophenyl)-2-hydroxybutyl-1-(4-methylphenyl) sulfonate.

EXAMPLE 6

To a 100 ml round bottom flask was added 1.0076 g (0.00312 mole) of 4,4,4-trichloro-1,2-epoxy-2-(3,5-dichlorophenyl)butane, 1.3124 g (0.00690 mole) of p-toluenesulfonic monohydrate, 10 ml of benzene and 0.254 ml (0.00314 mole) of pyridine. The mixture, which forms a two-phase system at reflux, was heated at reflux for 3 hours and then cooled. The reaction mixture was washed twice with 10 ml portions of water and once with a 10 ml portion of 10 percent by weight NaHCO$_3$ and dried by filtration through anhydrous MgSO$_4$. The solvent was removed from the reaction mixture in vacuo and the resulting residual oil further dried at 50° C. under 2 mm Hg reduced pressure. A small sample of the oil analyzed by NMR showed a product containing the desired sulfonate and undesired butyraldehyde compound at a molar ratio of 91 to 9.

The NMR sample was recombined with the remainder of the crude product and the entire quantity taken up in 2 ml of methylcyclohexane. On cooling the methylcyclohexane, a white crystalline product precipitated and was isolated, providing 1.2165 g of the desired sulfonate having a melting point of 107° to 109° C.
Comparison Run To a round bottom flask was added 1.0071 g (0.003143 mole) of 4,4,4-trichloro-1,2-epoxy-2-(3,5-dichlorophenyl)butane, 0.6543 g (0.003440 mole) of p-toluenesulfonic acid monohydrate, and 10 ml of benzene. Reaction and initial analysis were carried out as in Example 6. Analysis showed that the reaction product was mainly the undesired butyraldehyde.

EXAMPLE 7

Into a 100 ml round bottom flask was placed 0.9992 g (0.003119 mole) of 4,4,4-trichloro-1,2-epoxy-2-(3,5-dichlorophenyl) butane, 1.3155 g (0.006164 mole) of p-toluenesulfonic acid monohydrate, 0.254 ml (0.003140 mole) of pyridine and 10 ml of cyclohexane.

Reaction under reflux and work up of the reaction product was carried out in the same manner as in Example 6. The desired sulfonate compound in the form of purified product was obtained in the amount of 0.9910 g having a melting point of 104° to 106° C. Analysis of the crude product showed a molar ratio between the desired sulfonate and the undesired butyraldehyde to be 49 to 21 with about 21 percent of the epoxybutane starting material unreacted.

EXAMPLE 8

Into a 100 ml round bottom flask was placed 1.0056 g (0.003139 mole) of 4,4,4-trichloro-1,2-epoxy-2-(3,5-dichlorophenyl)butane, 1.3164 g (0.006921 mole) of p-toluenesulfonic acid monohydrate, 0.254 ml (0.003140 mole) of pyridine and 10 ml of carbon tetrachloride. Reaction was conducted at reflux for 2 hours, the reactants forming a two-phase system at reflux which could not be well mixed with a stirring bar.

The reaction mixture was washed once with a 15 ml portion of 10 percent by weight aqueous NaHCO$_3$ solution and once with a 10 ml portion of water and then dried by filtration through both anhydrous Na$_2$SO$_4$ and MgSO$_4$. NMR analysis of the filtrate showed 65 percent completion of the reaction and a molar ratio between the desired sulfonate and undesired butyraldehyde compound of 83 to 17.

The aqueous washes were extracted with 5 ml of CCl$_4$ and the extract was also dried by passing it through Na$_2$SO$_4$ and MgSO$_4$. The dried extract was combined with the washed and dried CCl$_4$ layer from the reactant mixture. To the combined CCl$_4$ solutions was added 15 ml of n-pentane and the mixture stirred causing precipitation of a crystalline product. The mixture was cooled to $-8°$ C. resulting in additional precipitation of a white crystalline product that was recovered by filtration and dried, yielding 0.5782 grams of the desired sulfonate having a melting point of 109.5° to 111° C.

EXAMPLE 9

Into a 3 ml reaction vial was placed 50.2 milligrams (mg) (0.1567 mmole) of 4,4,4-trichloro-1,2-epoxy-2-(3,5-dichlorophenyl)butane, 96.7 mg (0.5084 mmole) of p-toluenesulfonic acid monohydrate, 0.5 ml of benzene and 25.3 microliters ($\mu$l) (0.3128 mmole) of pyridine.

The reaction mixture was heated at 85° C. with stirring for 4 hours. The two-phase system was then cooled and the layers separated. The organic layer was washed with two 1 ml portions of water. The aqueous layer was extracted with one 0.5 ml portion of benzene. The benzene extract was washed with 1 ml of 10 percent by weight aqueous NaHCO$_3$ solution and filtered through anhydrous MgSO$_4$ and Na$_2$SO$_4$ into a small round bottom flask. The aqueous sodium bicarbonate washing was extracted four times with 0.5 ml portions of benzene and each such portion was also passed through the anhydrous MgSO$_4$ and Na$_2$SO$_4$ and combined with the previous benzene extract.

The benzene was then flashed off in vacuo leaving 72.0 mg of a colorless oily film which was taken up in 1 ml of ether. Then 2 ml of n-hexane was added and the resulting mixture stirred under nitrogen and concentrated to about 1 ml resulting in precipitation of a crystalline product. Yet an additional 1 ml of n-hexane was added and the mixture again concentrated to about 1 ml. The solvent was removed with a filter stick and the precipitate was rinsed with 1 ml of n-hexane and then dried in vacuo resulting in 59.7 mg of 4,4,4-trichloro-2-(3,5-dichlorophenyl)-2-hydroxybutyl-1-(4-methylphenyl)sulfonate in the form of a white crystalline solid melting at 108.5° to 109.5° C. in 77.3 percent yield based on the amount of epoxybutane reactant.

EXAMPLE 10

To a 3 ml reaction vial was added 1.0045 g (0.003135 mole) of 4,4,4-trichloro-1,2-epoxy-2-(3,5-dichlorophenyl)butane and 255 $\mu$l (0.003153 mole) of pyridine forming an orange solution. To this was added 1.2574 g (0.006611 mole) of p-toluenesulfonic acid monohydrate which gradually dissolved to form a two-phase system. The mixture was heated in an 85° C. oil bath for 4 hours, the two-phase system remaining throughout. The mixture was allowed to cool and stand overnight.

Analysis of both layers by reverse phase high pressure liquid chromatography showed that all of the epoxybutane had reacted.

The reaction mixture was taken up in a diethylether-water mixture and transferred to a 10 ml separatory funnel. The vial was rinsed with several additional portions of diethylether-water, a total of 15 ml of diethylether and 10 ml of water was used for the transfer. The phases were mixed and allowed to separate and the water layer was removed. The diethylether layer was washed with one 10 ml portion of water and one 10 ml portion of 10 percent aqueous NaHCO$_3$ solution. The aqueous washings were combined and extracted with 10 ml of diethylether. The ether extract was combined with the previously washed ether solution and the entire amount dried by filtering through anhydrous MgSO$_4$. Analysis by high pressure liquid chromatography showed that the major component of the ether solution was desired sulfonate.

The ether solution was then concentrated in vacuo, diluted with n-hexane and the solvent removed in vacuo leaving a viscous yellow oil. A small sample was removed for NMR analysis and recombined using diethylether for the transfer. The solvent was removed in vacuo and the residue recrystallized from 2 ml of methylcyclohexane. The methylcyclohexane solution was cooled to $-10°$ C. resulting in formation of a white precipitate. The supernatant liquid was removed with a filter stick and the precipitate washed three times with 2 ml portions of n-pentane and dried in vacuo to afford 1.080 grams (70 percent yield) of the desired sulfonate having a melting point 105° to 107° C.

EXAMPLE 11

Into a 50 ml round bottom flask was placed 1.2634 g (0.006642 mole) of p-toluenesulfonic acid monohydrate and a stirring bar and the hydrated material heated at 60° C. over P$_2$O$_5$ at 0.5 mm Hg partial pressure for 2 hours. The white crystalline solid changed to a violet colored liquid within $\frac{1}{2}$ hour.

The vacuum was replaced with dried nitrogen and 10 ml benzene was added, forming a homogeneous solution. Thereafter, addition of 0.255 ml (0.003153 mole) of pyridine caused only light precipitation. Upon addition of 1.0074 g (0.003144 mole) of 4,4,4-trichloro-1,2-epoxy-2-(3,5-dichlorophenyl)butane afforded initially a homogeneous solution followed by separation of the mixture into two phases.

The two-phase mixture was heated to reflux and became homogeneous within one hour. After 4 hours, heating was stopped and the reaction mixture was allowed to cool and stand overnight.

The reaction mixture was treated with 10 ml of water, mixed well and transferred to a separatory funnel. The reaction flask was rinsed with 5 ml of benzene and the rinsing added to the separatory funnel. The phases were mixed and separated. The benzene layer was washed with one 10 ml portion of water and one 10 ml portion of 10 percent by weight aqueous NaHCO$_3$ solution. The combined aqueous washings were extracted once with 10 ml of benzene and the benzene extract combined with the previously separated and washed benzene solution and the combined benzene solutions dried by filtration through anhydrous MgSO$_4$. The solvent was removed in vacuo and the residual oil taken up in 10 ml of CCl$_4$ and again concentrated in vacuo to remove the last traces of benzene. The residual oil was again dissolved in 5 ml of CCl$_4$ and a sample taken for an NMR analysis which showed the molar ratio of desired sulfonate to undesired butyraldehyde compound to be about 96 to 4.

Again the solvent was removed in vacuo and the oil taken up in 3 ml of methylcyclohexane and cooled to precipitate the white crystalline product. The product was washed twice with 2 ml portions of n-pentane and dried leaving 1.3516 g of the desired sulfonate having a melting point of 107° to 109° C. An 87.3% yield of product was thus isolated.

Comparison Run

In a procedure quite similar to Example 11 0.6526 g (0.003431 mole) of p-toluenesulfonic monohydrate was dried and thereafter combined with 10 ml benzene and 25 μl (0.000309 mole) of pyridine and reacted at reflux in the same manner as described in Example 11. NMR analysis of the crude product resulting from this reaction showed a molar ratio of 2 to 98 for the desired sulfonate to the undesired butyraldehyde, showing that formation of the aldehyde is favored under these conditions.

EXAMPLE 12

To a 50 ml round bottom flask was added 1.2649 g (0.006650 mole) of p-toluenesulfonic acid monohydrate and drying operations were carried out as described in Example 11. Thereafter to the flask was added 10 ml of methylene chloride, 0.255 ml (0.003153 mole) of pyridine and 1.0076 g (0.003129 mole) of 4,4,4-trichloro-1,2-epoxy-2-(3,5-dichlorophenyl)butane. The reaction mixture was heated at reflux in the manner described in Example 11. The reaction was followed by periodic sampling for NMR analysis which showed the reaction to be 50 percent, 86 percent and 90 percent complete after 3 hours, 8 hours and 12 hours at reflux, respectively. After 12 hours, the reaction mixture was cooled and the crude product isolated as described in Example 11.

The crude oily product was taken up in about 3 ml of diethylether to which was added 7 ml of n-hexane and the mixture concentrated under nitrogen with stirring to about 5 ml resulting in precipitation of white crystalline product. The supernatant liquid was removed and the precipitate was rinsed twice with 2 ml portions of n-hexane and dried, providing 1.129 g (73 percent yield) of the desired sulfonate as a white solid melting at 107° to 109° C.

EXAMPLE 13

Into a 250 ml round bottom flask was placed 11.6 g (0.0609 mole) of p-toluenesulfonic acid monohydrate and 120 ml of benzene and slurried together. The slurry was heated at reflux with a Dean-Stark trap to remove the water of hydration. After about 1.2 hours, about 1.5 ml of water had collected and the anhydrous acid had become soluble in the benzene. The solution was cooled to 55° C. and 2.41 g (0.0305 mole) of pyridine and 3 ml additional benzene were added and then 8.44 g (0.0277 mole) of 2-(2,2,2-trichloroethyl)-2-(3-chloro-5-fluorophenyl)oxirane and yet 15 ml additional benzene. The cloudy reaction mixture was heated at reflux for 4.5 hours, becoming homogeneous. The solution was allowed to stir at room temperature overnight with the pyridine salt of p-toluenesulfonic acid crystallizing out.

The slurry was diluted with about 75 ml of benzene and then washed three times with 150 ml portions of water, a 200 ml portion of 5 percent by weight aqueous NaHCO$_3$ solution, and finally a 150 ml portion of 9.1 percent by weight hydrochloric acid. The organic layer was separated and dried with Na$_2$SO$_4$ and the solvent removed in vacuo leaving 11.9 grams of crystalline product.

The product was taken up in 25 ml of methylcyclohexane at reflux temperature. The solution was allowed to cool and then stirred at room temperature for about an hour, resulting in precipitation of a white crystalline product which was collected by filtration and washed twice with 15 ml portions of hexane and dried at 80° C. in vacuo. 10.5 g of white crystalline product melting at 112.5° to 114.5° C. and identified as 4,4,4-trichloro-2-(3-chloro-5-fluorophenyl)-2-hydroxybutyl-1-(4-methylphenyl)sulfonate was obtained. Elemental analysis showed the following:

Calculated: % C, 42.8; % H, 3.18; Found: % C, 42.8; % H, 3.22.

EXAMPLE 14

In a 250 ml round bottom flask was slurried 11.0 g (0.0579 mole) of p-toluenesulfonic acid monohydrate in 120 ml of benzene. The slurry was heated at reflux and a Dean-Stark trap was used to remove about 1.0 ml of water. After about 1.5 hours, the mixture was a homogeneous solution. The solution was cooled and a Dean-Stark trap removed from the system. When the flask and contents were at 55° C., there was added 2.29 g (0.0289 mole) of pyridine, 3 ml additional pyridine followed by 9.3 g (0.0263 mole) of 2-(3-chloro-5-trifluoromethylphenyl)-2-(2,2,2-trichloroethyl)oxirane in 15 ml of benzene. The cloudy mixture was heated at reflux for 4.5 hours becoming clear as the reaction proceeded. The reaction mixture was cooled to and stirred at room temperature overnight with the p-toluenesulfonic acid-pyridine salt precipitating.

The reaction mixture was diluted with about 100 ml of benzene and then washed twice with 200 ml portions of water, once with a 200 ml portion of 5 percent by weight aqueous NaHCO$_3$ solution and then a 200 ml portion of 9.1 percent by weight hydrochloric acid. The organic layer was separated and dried with a mixture of anhydrous Na$_2$SO$_4$ plus powdered charcoal. The charcoal did not decolorize the orange colored solution. The solvent was then removed from the product mixture in vacuo leaving an oil which was held at 55° C. under less than 3 mm Hg partial pressure for 1 hour, and on cooling and scratching, crystallization took place yielding 12.7 grams of crude solid.

The crude product was recrystallized from methylcyclohexane. This was done by taking up the solid initially in 25 ml of methylcyclohexane in reflux temperature. On cooling and scratching the receptacle, an oil initially separated but became crystalline and as crystallization proceeded the slurry became quite thick. Another 10 ml of methylcyclohexane was added and the slurry stirred at room temperature for about 1 hour after which the white crystalline product was collected by filtration and washed with 225 ml portions of hexane and air dried overnight, yielding 10 grams of material melting at 87° to 88° C. NMR analysis and elemental analysis confirmed the product to be 4,4,4-trichloro-2-(3-chloro-5-(trifluoromethyl)phenyl)-2-hydroxybutyl-1-(4-methylphenyl)sulfonate.

Calculated: % C, 41.08; % H, 2.87; Found: % C, 41.01; % H, 2.90.

EXAMPLE 15

In a 250 ml round bottom flask was placed 14.3 g (0.0521 mole) of 4-sulfophenoxy acetic acid isopropyl ester and 100 ml of benzene, which formed a slurry. The slurry was heated at reflux with a Dean-Stark trap in the system and about 20 ml of liquid was collected in the trap. The contents of the trap were slightly cloudy suggesting a small amount of water had come over. The acid nonetheless remained insoluble at reflux and the mixture was cooled to about 55° C. at which temperature 2.08 g (0.0263 mole) of pyridine and 3 ml of benzene was added, the entire mixture becoming homogeneous. To this solution was added 8.0 g (0.0250 mole) of 2-(3,5-dichlorophenyl)-2,2,2-trichloroethyloxirane and the resulting mixture heated at reflux for 4 hours and then cooled.

The reaction mixture was washed with three 100 ml portions of water. On attempting to dry the organic layer by passing it through anhydrous $Na_2SO_4$, the product commenced to crystallize and therefore acetone was added to dissolve the product and remove it from the particulate $Na_2SO_4$. The solvent was removed from the solution in vacuo leaving a white crystalline product which was further dried at 80° C. in vacuo, providing 13.5 g of crude product. The crude product was slurried in 25 ml of benzene and heated to reflux whereupon most of the product dissolved. On cooling, the product started to crystallize and after stirring for about 1 hour the precipitate was collected by filtration and washed two times with 25 ml portions of hexane and dried at 80° C. in vacuo, resulting in 9.5 g of purified product melting at 147° to 149° C. The NMR spectrum of the purified product was consistent with the structure of the desired product, 4,4,4-trichloro-2-(3,5-dichlorophenyl)-2-hydroxybutyl-1-(4-(1-methylethoxy)carboxymethoxyphenyl)sulfonate. This was further confirmed by elemental analysis.

Calculated: % C, 42.41; % H, 3.56; Found: % C, 42.45; % H, 3.52.

EXAMPLE 16

In a three liter flask equipped with a stirrer, a condenser and a Dean-Stark trap were placed 327.2 g (1.72 mole) of p-toluenesulfonic acid monohydrate and 1,228.5 ml of benzene. The resulting thick slurry was heated at reflux for 22 hours until the theoretical amount of water of hydration had been collected in the Dean-Stark trap. The reaction mixture was then cooled to 30° C. and 66.3 ml (0.819 mole) of pyridine was added dropwise during one half hour period, with the reaction mixture becoming turbid. Then to the flask was added 262.3 g (0.819 mole) of 4,4,4-trichloro-1,2-epoxy-2-(3,5-dichlorophenyl)butane. The reaction mixture cleared, becoming homogeneous and a clear light yellow color as the reaction mixture was heated to reflux temperature. Refluxing was continued for 4 hours.

The reaction mixture was then cooled to about 60° C. and poured into a 6 liter separatory funnel and washed with 1300 ml of cold water, whereupon a white solid separated which was believed to be the pyridine salt of the sulfonic acid. The aqueous layer was separated and discarded and the benzene layer was washed a second time with 1300 ml of water, then with the 1300 ml portion of 5 percent by weight aqueous $NaHCO_3$ solution, and finally with 1375 ml of dilute aqueous HCl (25 ml of concentrated HCl per 100 ml of $H_2O$). The light yellow organic layer was separated and dried over anhydrous $Na_2SO_4$. The solvent was removed on a rotary evaporator leaving 430.3 g of a white crystalline solid which was dried in the vacuum oven at 70° C. for several hours and brought to a constant weight of 386 g (95.7 percent of theoretical yield). The dried white crystalline solid had a melting point of 103° to 106° C. and exhibited an NMR spectrum consistent with known spectra for the desired sulfonate product, viz., 4,4,4-trichloro-2-(3,5-dichlorophenyl)-2-hydroxybutyl-1-(4-methylphenyl)sulfonate.

The crude product was taken up in methylcyclohexane and reprecipitated therefrom upon cooling, the crystalline product being recovered by filtration. The collected solid was washed twice with 400 ml portions of n-hexane and then dried in a vacuum oven at 70° C. for about three hours, coming to constant weight. The resulting white crystalline solid exhibited a melting point of 110° to 111° C.

EXAMPLE 17

In a 250 ml, three-necked, round bottom flask equipped with a thermometer, a condenser and a Dean-Stark trap was placed a magnetic stirrer bar, 8.75 g (0.046 mole) of p-toluenesulfonic acid monohydrate and 50 ml of benzene. The thick slurry was heated and stirred at reflux for about 4 hours during which the theoretical amount of water of hydration was collected in the trap and the reaction mixture had become a solution. The flask and its contents were then cooled to about 30° C. and 1.74 g (0.0978 mole) of pyridine was added dropwise, the reaction mixture becoming turbid. Then 7.0 g (0.022 mole) of 4,4,4-trichloro-1,2-epoxy-2-(3-(trifluoromethyl)phenyl)butane was added to the flask and the reaction mixture was heated to reflux, the initial turbidity disappearing as the reaction mixture was heated to reflux, becoming homogeneous and a clear light yellow color. The reaction mixture was heated at reflux for 4 hours, cooled and poured into a separatory funnel. A white crystalline solid believed to be a pyridine salt of the sulfonic acid was observed.

The benzene layer was washed twice with 50 ml portions of water, once with a 50 ml portion of aqueous $NaHCO_3$ solution and once with a 50 ml portion of dilute aqueous hydrochloric acid containing 25 ml of concentrated HCl per 100 ml of water. The organic layer was recovered and dried over $Na_2SO_4$. The solvent was then removed on a rotary evaporator at a temperature of 50° C. The residual oil was maintained at 50° C. while the last traces of solvent were removed under reduced pressure. The oil was then taken up in methylcyclohexane, brought to reflux, cooled and stirrred, whereupon a white crystalline solid separated and was collected by filtration and washed with 210 ml portions of n-hexane, yielding 7.58 g of white crystalline solid having a melting point of 75° to 79° C. The product was subjected to elemental analysis, confirming that the product was 2-(3-trifluoromethylphenyl)-4,4,4-trichloro-2-hydroxybutyl-1-(4-methylphenyl)sulfonate.

Calculated: % C, 43.96; % H, 3.28; Found: % C, 44.0; % H, 3.37.

EXAMPLE 18

To illustrate the use of an acid-base equilibrium system, the following was performed:

A

To a round bottom flask was added 0.2023 g (0.631 mmole) of 4,4,4-trichloro-1,2-epoxy-2-(3,5-dichlorophenyl)butane; 0.1235 g (0.649 mmole) of p-toluenesulfonic acid; 0.1237 g (0.637 mmole) of sodium p-toluenesulfonate; and 2 ml of dimethylformamide. The reaction mixture was then stirred at 42° to 45° C. for 4 hours. The reaction mixture was then cooled and diluted with about 7 ml $H_2O$ and then extracted with about 0.5 ml $CCl_4$. The $CCl_4$ extract was washed with about 5 ml of 10 percent by weight aqueous $NaHCO_3$ solution and then with 5 ml H₂O before filtering through anhydrous MgSO₄. The washed extract was then analyzed by NMR and determined to contain about 3.5 percent of the desired 4,4,4-trichloro-2-(3,5-dichlorophenyl)-2-hydroxybutyl-1-(4-methylphenyl) sulfonate, whereas none of the undesired butyraldehyde was detected.

B

130 Cubic centimeters (cc) of toluene and 21 grams (g) of *p*-toluenesulfonic acid monohydrate were added together in a distillation apparatus and azeotroped dry. To this mixture was added 10 g of dimethylformamide and the resulting mixture was continued to be azeotroped dry. The mixture was then cooled and 32.9 g (0.1 mole) of 4,4,4-trichloro-1,2-epoxy-2-(3,5-dichlorophenyl)butane (97 percent pure) was added. The mixture was allowed to react at 80° C. After a 230 minute (min) reaction period, 0.0733 mole of 4,4,4-trichloro-2-(3,5-dichlorophenyl)-2-hydroxybutyl-1-(4-methylphenyl)sulfonate was formed as determined by high performance liquid chromatography (HPLC) analysis.

C

40 Grams of *p*-toluenesulfonic acid monohydrate in 100 cc of benzene was azeotroped dry under a 10 plate sieve tray column. To the mixture was added 18 g of dimethylformamide and the resulting mixture was continued to be azeotroped dry. The mixture was then cooled and 66 g (0.2 mole) of 4,4,4-trichloro-1,2-epoxy-2-(3,5-dichlorophenyl)butane (97 percent pure) was added. The mixture was then allowed to react at 80° C. The following quantities of 4,4,4-trichloro-2-(3,5-dichlorophenyl)-2-hydroxybutyl-1-(4-methylphenyl)-sulfonate were formed as determined by HPLC analysis for various reaction periods:

| Reaction Period | mole of desired product |
|---|---|
| 20 min | 0.0899 |
| 75 min | 0.127 |
| 130 min | 0.140 |
| 200 min | 0.147 |

Upon carrying out any of the foregoing examples in a similar manner but using any of the other above defined epoxides, strong acids, bases and organic solvents, in similar molar proportions, substantially the same desired results are obtained, minimizing aldehyde formation, and obtaining desired hydroxybutyl or hydroxypentyl product.

What is claimed is:

1. A method of preparing a 2-hydroxybutyl or 2-hydroxypentyl compound of the following formula:

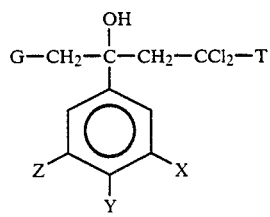

wherein:
T is F, Cl, Br, CH₃, CF₃ or

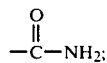

X, Y and Z are each independently H, F, Cl, Br, CH₃, C₂H₅, or CF₃, provided that when Y is other than H, at least one of X and Z must be other than H;

G is R¹SO₂O—; Br; Cl; F; or I; and

R¹ is C₁-C₁₈ alkyl; C₁-C₈ haloalkyl; C₃-C₆ cycloalkyl; benzyl; naphthyl; phenyl; monovalent radical of monocyclic heterocyclic ring having ring atoms selected from the group consisting of carbon and at least one of nitrogen, sulfur and oxygen; monovalent radical of bicyclic heterocyclic fused ring having a ring atoms selected from the group consisting of carbon and at least one of nitrogen, sulfur and oxygen; and any of phenyl, benzyl, naphthyl, said monocyclic heterocyclic radical or bicyclic heterocyclic fused ring radical in which up to three ring hydrogens have been replaced by substitutent groups which may be the same or different and are selected from the group consisting of methyl, methoxy, substituted methoxy, methylthio, chloro, bromo, fluoro, CF₃ or nitro;

which comprises:

reacting during a reaction period at a temperature in the range of about 20° to about 120° C. in the presence of an organic solvent an epoxide compound of the following formula:

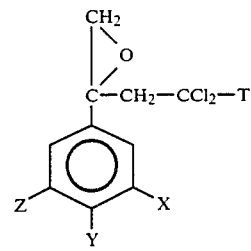

wherein:
T, X, Y and Z are as defined hereinabove;
with a proton source that is strong enough to protonate and catalyze the opening of the oxirane ring of said epoxide compound;
and with a nucleophile, the nucleophile being an anion and is selected from the group consisting of R¹SO₂O⁻; Cl⁻; Br⁶³; F⁻; or I⁻;
wherein R¹ is defined hereinabove;
the nucleophile being present in sufficient amount that substantial reaction takes place at the reaction temperature sufficient to avoid formation of more than about 50 mile percent of the theoretical maximum amount of an aldehyde compound of the following formula;

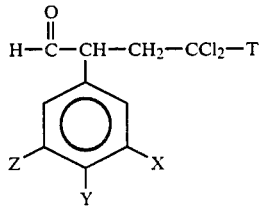

wherein T, X, Y, and Z are as defined hereinabove;

and said proton source provided throughout the reaction period in an amount sufficient to catalyze ring opening and facilitate reaction to form the desired 2-hydroxybutyl or 2-hydroxypentyl compound.

2. The method of claim 1 wherein said organic solvent is an inert organic solvent selected from the group consisting of acetonitrile, toluene, xylene, benzene, carbon tetrachloride, cyclohexane, chloroform, and methylene chloride.

3. The method of claim 1 wherein said organic solvent is an inert solvent selected from the group consisting of benzene, toluene, and acetonitrile.

4. The method of claim 1 wherein the proton source is a free strong acid selected from the group consisting of $R^1SO_2OH$; HBr; HCl; HF; and HI.

5. The method of claim 1 carried out in the presence of a strong base.

6. The method of claim 5 wherein said strong base is a tertiary amine, an alkali metal hydroxide or an alkali metal carbonate.

7. The method of claim 5 wherein the strong base is a tertiary amine.

8. The method of claim 7 wherein the tertiary amine is a triloweralkylamine.

9. The method of claim 7 wherein the tertiary amine is pyridine or dimethylaminopyridine.

10. The method of claim 1 wherein the proton source is derived from an equilibrium system comprising a free strong acid and a non-nucleophilic weak base in equilibrium with the respective deprotonated strong acid and protonated weak base.

11. The method of claim 10 wherein the free strong acid is selected from the group consisting of $R^1SO_2OH$; HBr; HCl; HF; and HI.

12. The method of claim 10 wherein the non-nucleophilic weak base is diphenyl amine; a tetraalkylurea; a dialkylamide; N-methyl-2-pyrrolidone; dimethyl acetamide; N-formylmorpholine; a lower alkyl phosphate; dimethylsulfone; tetramethylenesulfone; or hexamethylphosphoric triamide.

13. The method of claim 10 wherein the non-nucleophilic weak base is a dialkylamide.

14. The method of claim 10 wherein the non-nucleophilic weak base is dimethylformamide.

15. The method of claim 10 wherein the non-nucleophilic weak base is diphenyl amine.

16. The method of claim 1 carried out at a temperature in the range of about 40° to about 110° C.

17. The method of claim 1 carried out at a temperature in the range of about 80° to about 110° C.

18. The method of claim 1 wherein the amount of aldehyde formed is less than about 25 mole percent of the theoretical maximum amount of aldehyde.

19. The method of claim 1 wherein the amount of aldehyde formed is less than about 15 mole percent of the theoretical maximum amount of aldehyde.

20. The method of claim 1 wherein the proton source is p-toluenesulfonic acid.

21. The method of claim 10 wherein the free strong acid is p-toluenesulfonic acid.

22. The method of claim 4 wherein from about 1.5 to about 3 equivalents of the free strong acid are employed per equivalent of epoxide compound.

23. The method of claim 10 wherein from about 1.5 to about 3 equivalents of the proton source are employed per equivalent of epoxide compound.

24. The method of claim 22 wherein a strong base is employed at a concentration of from about 0.5 to about 2 equivalents of strong base per equivalent of epoxide compound, and the ratio of equivalents of free strong acid to equivalents of strong base is in the range of from about 1.25 to about 4.

25. The method of claim 23 wherein the concentration of non-nucleophilic weak base is at least 0.5 equivalents of weak base per equivalent of epoxide compound, and the ratio of equivalents of weak base to equivalents of free strong acid is at least 1.0.

26. The method of claim 25 wherein the ratio of equivalents of weak base to equivalents of free strong acid is at least 1.5.

27. The method of claim 4 wherein all of the reactants are not added initially and a strong base is employed at a concentration of from about 0.05 to about 1 equivalents of strong base per equivalent of epoxide compound, and the ratio of equivalents of free strong acid to equivalents of epoxide compound is in the range of from about 1 to 2 equivalents.

28. The method of claim 27 wherein the ratio of equivalents of free strong acid to equivalents of epoxide compound is about 1.1 equivalents.

29. The method of claim 20 wherein a tertiary amine is employed as a strong base.

30. The method of claim 29 wherein X and E are chloro and Y is H.

31. The method of claim 30 wherein T is chloro.

32. The method of claim 21 wherein the non-nucleophilic weak base is dimethylformamide.

33. The method of claim 32 wherein X and Z are chloro and Y is H.

34. The method of claim 33 wherein T is chloro.

35. The method of claim 27 wherein the free strong acid is added in portions as at least several or more small additions.

36. The method of claim 27 wherein the free strong acid is added substantially continuously throughout the period of time from about 1 to 4 hours.

* * * * *